United States Patent [19]

Medwid

[11] Patent Number: 4,747,393
[45] Date of Patent: May 31, 1988

[54] VISCERAL RETRACTOR

[76] Inventor: Albert Medwid, 2320 Bath St., Santa Barbara, Calif. 93105

[21] Appl. No.: 455,811

[22] Filed: Jan. 5, 1983

[51] Int. Cl.⁴ ............................................. A61B 17/02
[52] U.S. Cl. ...................................................... 128/20
[58] Field of Search .................. 128/15, 16, 20, 87 R, 128/89 R, 90, DIG. 19; 2/243 B

[56] References Cited

U.S. PATENT DOCUMENTS 206,584  7/1878  Lawson ............................... 2/243 B

FOREIGN PATENT DOCUMENTS 1604168  12/1981  United Kingdom .................. 128/15

OTHER PUBLICATIONS

Hospital Supplies, V. Mueller & Co., Catalogue No. 65, 1963, McNealy et al., FIG. D.

*Primary Examiner*—Max Hindenburg
*Attorney, Agent, or Firm*—Pretty, Schroeder, Brueggemann & Clark

[57] ABSTRACT

An improved visceral retractor is provided for use by a surgeon during closure of a surgical incision or the like. The visceral retractor comprises an elongated, relatively thin sheet of flexible plastic or rubber-based material having a generally fishlike shape to include a generally oval body portion joined by a relatively narrow waist region to a comparatively small tail portion. Either the body portion or the tail portion is insertable through an incision, depending upon the size of the incision, to separate underlying internal organs from overlying tissue thereby preventing the organs from bulging into the incision or from being sutured as the incision is closed. With a relatively large incision, the body portion may be inserted during initial suturing until the incision is closed to a smaller size, whereupon the retractor is reversed and the tail portion is inserted during further suturing. In one form of the invention, the visceral retractor is imprinted with contoured pattern lines indicating smaller sizes to which the retractor may be cut for use with smaller incisions.

8 Claims, 1 Drawing Sheet

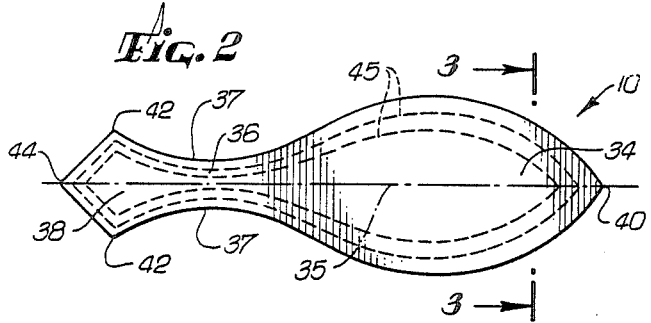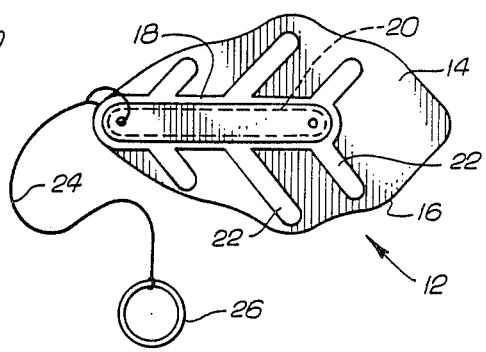
Fig. 1 PRIOR ART
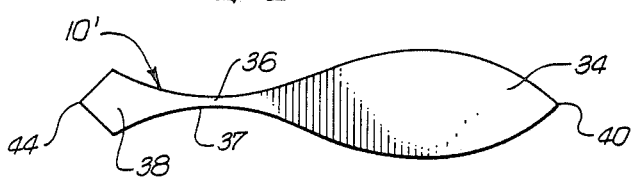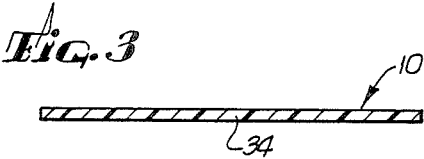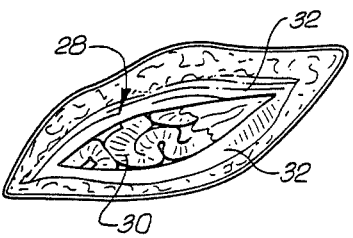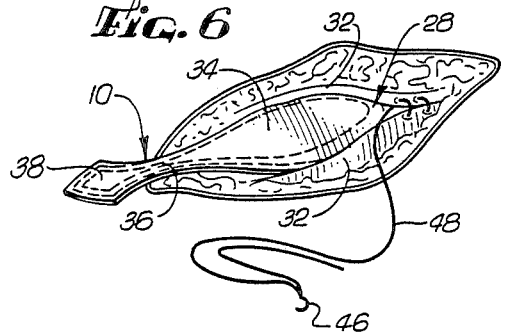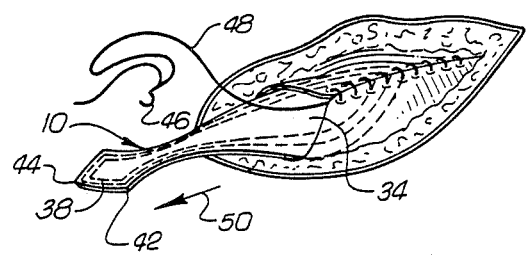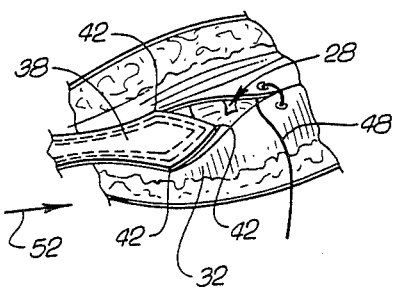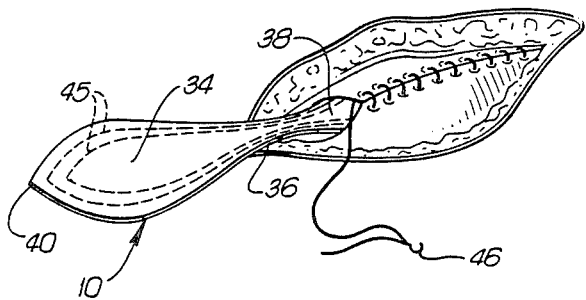

VISCERAL RETRACTOR

BACKGROUND OF THE INVENTION

This invention relates generally to medical products for use during surgical procedures. More particularly, this invention relates to an improved so-called visceral retractor for protecting internal patient organs during closure of a surgical incision or the like.

In many types of surgical procedures, such as abdominal surgery, an incision is made through several outer tissue layers to gain access to internal patient organs, such as the intestines or the like. At the conclusion of the surgery, the tissue layers are sutured to close the incision. However, particularly with abdominal surgery, incision suturing can be a difficult and tedious procedure, since the underlying internal organs may bulge upwardly into the incision. This undesirably exposes the organs to possible damage from puncture during the suturing process and further subjects partially sutured tissue layers to stress which can cause tearing.

There exists, therefore, a need for a surgical device or appliance which can be used to separate internal patient organs from overlying tissue layers during incision closure at the conclusion of a surgical procedure. Such a device, referred to as a visceral retractor, must be adapted for relatively easy insertion through the incision to a position immediately underlying the tissue layers. In this position, the retractor must be capable of being held easily by the surgeon to retract patient organs from the incision without interferring with the suturing process and further must be adapted for removal from the patient after the incision is substantially closed. Moreover, the visceral retractor is desirably provided in a form which is inexpensive to manufacture, easy to sterilize, capable of use with incisions of different sizes, and preferably disposable after use.

One visceral retractor presently on the market is provided in the form of a generally oval flexible plastic or rubber-based sheet for insertion through the incision between overlying tissue layers and underlying patient organs. The oval sheet is structurally reinforced by a central metal bar and by thickened ribs radiating therefrom for retracting patient organs from the incision, and a string or the like is attached to one end of the retractor to support a plastic safety ring outside the incision to prevent the retractor from being left inadvertently within the patient. While visceral retractors of this type perform satisfactorily during initial closure of a relatively large incision, they must be removed from the patient relatively early in the suturing procedure to avoid being trapped within the patient, thereby leaving a substantial portion of the suturing process to be performed without the assistance of a visceral retractor or requiring the use of a separate device such as a handheld metal bar, to separate the overlying tissue layers from the underlying organs, for the final four-to-five inches of suturing. Moreover, it has been found that the string and safety ring tend to shift about and interfere with the suturing process.

The present invention overcomes the problems and disadvantages of the art by providing an improved visceral rectractor which is specifically shaped for use throughout a suturing process until the incision is substantially closed. The invention is thereby also usable with large and small incisions to eliminate any requirement to provide several retractors of different sizes.

SUMMARY OF THE INVENTION

In accordance with the invention, an improved visceral retractor is provided for use by a surgeon during suturing of an incision formed through tissue layers overlying internal patient organs, such as at the conclusion of abdominal surgery or the like. The visceral retractor separates the underlying organs from the tissue layers and is easily held by the surgeon to bear downwardly with slight pressure on the organs to retract the organs from the incision. This permits suturing of the incision without fear of suturing the organs and further without applying any significant pressure to the incision during suturing which could otherwise cause tissue tearing. Importantly, the improved visceral retractor of this invention is specifically shaped for use substantially throughout the suturing process and for use with incisions of different size.

In a preferred form, the improved visceral retractor comprises an elongated and relatively thin sheet of flexible plastic or pliable rubber-based elastomer material having sufficient structural thickness and integrity to separate and space underlying organs from overlying tissue layers. The visceral retractor has a generally fishlike shape to include at one end a relatively large and generally oval or elliptically-shaped body portion joined by a relatively narrow waist region to a comparatively smaller, and relatively short tail portion having a generally triangular configuration at the opposite end of the retractor. Either the body portion or the tail portion is insertable through the incision to separate the underlying organs from the overlying tissue layers, depending upon the size of the incision, with the other portion projecting out of the incision and functioning as a convenient handle for adjusting the position of the retractor as the incision is closed. With relatively large incisions, the body portion is first inserted during initial closure until the incision is reduced to a relatively small size whereupon the body portion is withdrawn and the tail portion is inserted for use until the incision is substantially closed. The triangular configuration of the tail portion, which includes an apex corner presented in a direction away from the body portion, permits gradual withdrawal of the tail portion from the incision as the incision is reduced in size thereby protecting the underlying organs substantially until the incision is completely closed.

The visceral retractor of this invention is relatively inexpensive to manufacture and is readily provided in a sterilized package and disposable subsequent to use. The retractor shape permits use with large or small incisions, and in accordance with a preferred form, the retractor may further include visible pattern markings on one side indicating outlines to which the retractor may be cut to a smaller size if desired, thereby avoiding any requirement to purchase and stock visceral retractors of different sizes.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a plan view of a prior art visceral retractor;

FIG. 2 is a plan view of an improved visceral retractor embodying the novel features of the present invention;

FIG. 3 is an enlarged cross section of the visceral retractor taken generally on the line 3—3 of FIG. 2;

FIG. 4 is a plan view illustrating the visceral retractor of FIG. 2 trimmed to a smaller size;

FIG. 5 is a perspective view illustrating, somewhat in schematic form, an abdominal incision in a patient;

FIG. 6 is a perspective view illustrating use of the visceral retractor of the present invention during initial closure of the incision;

FIG. 7 is a perspective view illustrating withdrawal of the visceral retractor of this invention when the incision is partially closed;

FIG. 8 is a fragmented perspective view illustrating reversal and reinsertion of the visceral retractor of this invention for use during further closure of the incision; and FIG. 9 is a perspective view illustrating use of the visceral retractor of this invention during further closure of the incision.

DETAILED DESCRIPTION OF THE PREFERRED EMBODIMENT

As illustrated in the accompanying drawings, the present invention is embodied in an improved visceral retractor referred to generally by the reference numeral 10 for use in separating underlying patient organs from overlying tissue layers during suturing of an incision in the tissue layers at the conclusion of a surgical procedure. The visceral retractor 10, which is specifically geometried for use with incisions of different size and for use substantially throughout the suturing process, prevents the underlying patient organs from bulging into the incision where they could otherwise apply pressure to the incision or inadvertently be sutured to the tissue layers as the incision is closed.

The visceral retractor 10 of this invention provides a significant advance over presently available visceral retractors 12 of the type shown in FIG. 1 and sold by Adept-Med, Inc. of San Jose, California. This illustrative visceral retractor 12 comprises a relatively thin and somewhat flexible plastic or rubber-based sheet 14 having a generally elliptical shape defined by a somewhat irregular peripheral contour 16. The sheet 14 is reinforced by a central, longitudinally extending rib 18 into which a stiffening member 20, such as a stainless steel rod, is inserted, together with a plurality of outwardly radiating secondary ribs 22 of increased thickness relative to the sheet to improve the overall structural rigidity of the retractor. A safety line 24 is attached to one end of the central rib 18 and carries at its opposite end a relatively large safety ring 26.

In use, the prior art visceral retractor 12 shown in FIG. 1 is inserted into and through a surgical incision 28, as viewed in FIG. 5, formed in tissue layers in the course of a surgical procedure. For example, in abdominal surgery, the incision 28 may be formed in the tissue layers overlying internal organs, such as the intestines 30 as illustrated in FIG. 5, wherein the tissue layer immediately overlying the intestines 30 comprises the posterior rectus sheath 32. The retractor 12 is interposed between the sheath 32 and the intestines 30 to provide a separation or barrier wall which can be held down with slight pressure by the surgeon to retract the intestines from the incision 28 during suturing of the incision at the conclusion of the surgical procedure. The safety line 24 and ring 26 remain outside the incision as a visible reminder to remove the visceral retractor from the patient before concluding the suturing process. However, the size and shape of the prior art visceral retractor 12 permits its use only with relatively large incisions and requires withdrawal of the retractor while the incision is still relatively large, thereby requiring a significant portion of the incision to be closed without the aid of a visceral retractor of alternatively requiring the use of a separate device such as a hand-held metal bar, to separate the overlying tissue layers from the underlying organs, for the final four-to-five inches of suturing.

The visceral retractor 10 of this invention is shown in detail in FIGS. 2-4. As illustrated, the retractor 10 comprises a relatively simple unitary construction in the form of a relatively thin, elongated sheet of pliable elastomer or plastic material, such as silastic rubber, polyethylene, polypropylene, or the like, which can be inexpensively shaped or molded and is readily sterilized for surgical use. The elongated sheet is shaped to have a generally fishlike configuration formed symmetrically about a central longitudinal axis 35 to include at one end a generally oval or elliptical-shaped body portion 34. The body portion is oriented with its major axis coinciding generally with the longitudinal axis 35 of the retractor and is sized and shaped to extend approximately over about one-half or more of the retractor length. One end of this body portion 34 blends with a relatively short and relatively narrow waist region 36 defined by outwardly concave and smoothly contoured edges 37 which is in turn joined to a relatively short tail portion 38 having a generally triangular configuration, with a transverse dimension comparatively smaller than the transverse width of the body portion 34.

While the particular dimensions of the visceral retractor 10 may be varied in accordance with a given set of design parameters, a thickness of about one-sixteenth inch and an overall length on the order of about one foot is preferred. In a retractor of this length, the body portion 34 has a generally elliptical shape with a major axis extending preferably from a front tip 40 for a distance of about six to eight inches and a minor axis sized on the order of about four to six inches. The waist region 36 blends smoothly with one end of the body portion and is disposed symmetrically about the longitudinal axis 35 with a transverse width of about one to about one and one-half inches and blends into the triangular tail portion 38. The tail portion 38 includes a pair of oppositely directed, symmetrically formed base corners 42 spaced from each other by about two to about three inches and an apex corner 44 formed generally on the axis 35 and extending in a direction away from the body portion 34.

In accordance with one primary aspect of the visceral retractor 10 of this invention, a series of contoured pattern lines 45 is imprinted on one side of the retractor at spaced intervals from the peripheral contour of the retractor. These pattern lines 45 provide guide lines for trimming the retractor 10 to a similar geometry of smaller size by use of scissors or the like (not shown), as illustrated by the retractor 10' in FIG. 4. Such trimming may be desirable, for example, when the retractor is used during closure of a small incision, such as may be made in the course of a surgical procedure on a child.

The visceral retractor 10 of this invention is inserted through an incision at the conclusion of a surgical procedure, as illustrated in FIGS. 5–9 with respect to the incision 28 in a posterior rectus sheath 32 and other tissue layers overlying internal organs, such as intestines 30. When the incision 28 is relatively large, the relatively large body portion 34 is first inserted to a position between the sheath 32 and the underlying intestines 30 where, with slight pressure as may be applied by the surgeon's thumb (not shown), the retractor prevents the intestines from bulging or protruding into the incision and provides a barrier wall of sufficient thickness and stiffness to permit the incision 28 to be sutured quickly and easily as by use of a suturing needle 46 and thread 48 or the like without fear of puncturing, piercing, or suturing the underlying intestines. Moreover, the intestines do not apply any pressure to the partially sutured sheath which could otherwise cause tearing of the tissues.

The body portion 34 of the visceral retractor is withdrawn gradually from the incision 28 during the suturing process, as viewed in FIGS. 6 and 7, using the conveniently accessible tail portion 38 as a handle member which projects outwardly from the incision. When the size of the incision is reduced to a point where the sheath 32 cannot be sutured over the body portion without stretching the tissue, the retractor 10 is withdrawn from the incision, as depicted by arrow 50 in FIG. 7. The retractor 10 is then reversed in orientation and the tail portion 38 is inserted through the incision to a position beneath the sheath 32 and overlying the intestines 30, as illustrated by arrow 52 in FIG. 8. The relatively smaller tail portion 38 is then used to protect the underlying organs and is withdrawn gradually from the incision using the body portion 34 as a handle member as the suturing process continues nearer to its conclusion, as shown in FIG. 9. Importantly, the diamond-like configuration of the tail portion 38 provides a progressively smaller transverse width as it is withdrawn from the incision so that the retractor can be used to protect the underlying organs virtually until the last stitch in the suturing process.

The visceral retractor 10 of this invention thus provides a simple, inexpensive, and highly versatile retractor structure which can be provided in one size in a sterilized package for use during closure of large or small incisions. If desired, the retractor can be trimmed along a selected pattern line 45 to a smaller size before or during use, thereby avoiding any need to provide retractors of different sizes. The retractor is usable substantially throughout the process of closing an incision to protect and space underlying organs from a tissue layer being sutured, following which the retractor 10 may be discarded.

A variety of modifications and improvements to the visceral retractor described herein are believed to be apparent to one skilled in the art. Accordingly, no limitation of the invention is intended by way of the description herein, except as set forth in the appended claims.

I claim:

1. A visceral retractor for insertion through a surgical incision formed in tissue layers overlying internal patient organs to a position between the overlying tissue layers and the underlying internal organs to retract the organs from the incision and to protect the organs from being sutured during closure of the incision, the visceral retractor comprising:

an elongated, thin sheet of flexible material formed generally symmetrically about a central longitudinal axis to include a body portion of generally oval configuration at one end of said sheet with its major axis generally coinciding with said longitudinal aixs, a tail portion of generally triangular shape at the opposite end of said sheet with an apex corner disposed generally on said longitudinal axis and projected in a direction away from said body portion, said tail portion further including a pair of base corners spaced symmetrically on opposite sides of said longitudinal axis and spaced from each other by a distance less than the length of the minor axis of said body portion, and a waist regiion intermediate said body and tail portions, said waist region having smoothly contoured edges spaced symmetrically on opposite sides of said longitudinal axis and blending into said body portion and tail portion, said waist region having a transverse width less than the transverse widths of said body portion and said tail portion;

wherein said sheet is formed to have an overall length of about one foot and a thickness on the order of about one-sixteenth inch, said body portion having a major axis of about six to eight inches and a minor axis of about from four to six inches, said smoothly contoured edges of said waist region being spaced from one another by about one to one and one-half inches, and said tail portion base corners being spaced from each other by about two to three inches.

2. The visceral retractor of claim 1 wherein said smoothly contoured edges of said waist region have a concave configuration presented outwardly from said longitudinal axis and joining said tail portion at said base corners.

3. The visceral retractor of claim 1 wherein said sheet is formed from a flexible material having sufficient thickness and structural rigidity to retract the organs from the incision and to provide a protective barrier between the organs and the overlying tissue layers to prevent inadvertent suturing of the organs during closure of the incision in the tissue layers.

4. The visceral retractor of claim 1 wherein the length of the major axis of said body portion is at least about one-half the overall length of said sheet.

5. The visceral retractor of claim 1 wherein said sheet has pattern lines formed thereon at spaced intervals from the peripheral contour thereof to provide guides for trimming of said sheet to a selected smaller size of similar peripheral geometry.

6. A method of closing and suturing an incision formed in tissue layers overlying internal patient organs at the conclusion of a surgical procedure, the method using an elongated, thin sheet of flexible material having a generally oval body portion joined by a relatively narrow waist region to a tail portion having a length and width comparatively smaller than the body portion, comprising the steps of:

inserting the body portion through the incision to a position between the internal organs and the overlying tissue layers to provide a barrier therebetween and to retract the organs from the incision;

suturing the tissue layers to reduce the size of the incision to an extent substantially such that the body portion would be trapped beneath the tissue layers if suturing were continued;

withdrawing the body portion from the incision;

inserting the tail portion within the incision to a position between the internal organs and the overlying tissue layers to provide a barrier therebetween and to retract the organs from the incision;

resuming the suturing step to substantially close the incision; and withdrawing the tail portion of the retractor when suturing has progressed to a point that further suturing would prevent withdrawal of the tail portion.

7. The method of claim 6 wherein the retractor includes pattern lines thereon at spaced intervals from the peripheral contour thereof to provide guides for trimming of said sheet to a selected smaller size of similar peripheral geometry, and further including the step of trimming the retractor to a selected smaller size.

8. The method of claim 6 wherein the tail portion has a generally triangular shape with an apex corner presented away from the body portion and a pair of base corners spaced from one another, said step of withdrawing the tail portion from the incision comprising the step of gradually withdrawing the tail portion during the step of suturing the incision to a substantially closed condition.

* * * * *